US00PP34359P2

(12) United States Plant Patent
Hansen

(10) Patent No.: US PP34,359 P2
(45) Date of Patent: Jun. 21, 2022

(54) ***HIBISCUS* PLANT NAMED 'EDGE OF NIGHT'**

(50) Latin Name: ***Hibiscus* hybrid (L.)**
Varietal Denomination: Edge of Night

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 17/300,863

(22) Filed: Nov. 29, 2021

(51) Int. Cl.
*A01H 5/02* (2018.01)
*A01H 6/60* (2018.01)

(52) U.S. Cl.
USPC ..... Plt./257
CPC ..... *A01H 6/608* (2018.05)

(58) Field of Classification Search
USPC ..... Plt./257
CPC ..... A01H 6/608; A01H 5/02
See application file for complete search history.

*Primary Examiner* — Keith O. Robinson

(57) ABSTRACT

A new and distinct cultivar of winter-hardy, herbaceous, perennial, hybrid *Hibiscus* plant named 'Edge of Night' comprising a compact rounded mound habit of multiple, well-branched, basal stems producing flowers from the bottom to the top of the plant for five to six weeks from late July to early September. Flower petals are bubblegum pink with dark pink veins radiating toward margin and deep red eye set off with column of butter-yellow pollen. The foliage is mostly ovate, rarely trilobed, and very dark mahogany-colored.

2 Drawing Sheets

Botanical classification: *Hibiscus* hybrid (L.).
Variety denomination: 'Edge of Night'.

STATEMENT REGARDING PRIOR DISCLOSURES UNDER 37 CFR 1.77(B)(6)

The first publicly released non-enabling description was a photograph and brief description of the new plant was on Dec. 1, 2020 when it was placed on a website operated by Walters Gardens, Inc. Subsequently, the new plant had a non-enabling description and photograph in the "Walters Gardens 2021-2022 Catalog" first released on May 21, 2021. The first disclosure, in the form of a sale, was made by Walters Gardens, Inc. on Mar. 29, 2021. Walters Gardens, Inc. obtained the new plant and all information relating thereto, from the inventor. No plants of *Hibiscus* 'Edge of Night' have been sold, in this country or anywhere in the world, nor has any disclosure of the new plant been made, more than one year prior the filing date of this application, and such sale or disclosure within one year was either derived directly or indirectly from the inventor and would be 35 U.S.C § 102(b) exceptions.

BACKGROUND AND ORIGIN OF THE PLANT

The present invention relates to the new and distinct hardy, herbaceous, *Hibiscus* plant, *Hibiscus* 'Edge of Night' hybridized under direction of the inventor on Aug. 17, 2016 at a wholesale perennial nursery in Zeeland, Mich. The new plant is a single seedling selection from an intentional self-pollination of the complex, unreleased, proprietary hybrid known as 15-117-4 (not patented). Into the trial process the new plant was assigned the breeder code labeled 16-78-1. The parent has a complex mixture of species in them, comprising the species: *moscheutos* and *coccineus*.

*Hibiscus* 'Edge of Night' was first asexually propagated in late summer of 2018 by sterile shoot-tip tissue culture and later by greenhouse shoot tip cuttings at the same nursery in Zeeland, Mich. The resultant asexually propagated plants have been found to be stable and true to type in successive generations of asexual reproduction.

BRIEF SUMMARY OF THE PLANT

*Hibiscus* 'Edge of Night' differs from its parents as well as all other hardy herbaceous *Hibiscus* known to the applicant in many traits. The most similar *Hibiscus* known to the applicant are 'Airbrush Effect' U.S. Plant Pat. No. 29,295, 'Dark Mystery' U.S. Plant Pat. No. 32,036, 'Evening Rose' U.S. Plant Pat. No. 33,366, 'Perfect Storm' U.S. Plant Pat. No. 27,880, 'Holy Grail' U.S. Plant Pat. No. 31,478 and 'Mocha Moon' U.S. Plant Pat. No. 37,837. 'Airbrush Effect' has flowers of similar color but with more mottling, and the foliage is deeply dissected, tri-lobed, and dark green. 'Dark Mystery' is much taller and broader in habit, the foliage is wine-colored, and the flowers are pale to light pink with red eye. 'Evening Rose' has a larger habit, the foliage that is tri-lobed and mahogany colored, and the flower is more puckered and magenta-colored. 'Perfect Storm' has mostly tri-lobed foliage and flowers that are lighter pink in the middle with bright red eyes that radiates out in veins. 'Holy Grail' has a slightly larger habit, similar in foliage and the flowers are deep reddish-colored. 'Mocha Moon' has more cupped flowers with less pinkish color and reddish veins in the outer petal portion, the petals are more folded in the inner edge and the foliage is more tri-lobed.

The parent is taller and more upright in habit, the foliage tri-lobed and color was not as deep mahogany, and the flower is lighter pink.

*Hibiscus* 'Edge of Night' is a unique hardy herbaceous *Hibiscus* with the following combined traits:

1. Winter-hardy compact perennial with mounded habit of multiple, well-branched, basal stems.
2. Many flat rotate flowers produced from bottom to top of plant.
3. Flowers produced for about five to six weeks beginning mid-summer.
4. Flower petals of bubblegum pink with dark pink veining.
5. Flower has a deep red eye zone and delicate butter yellow pollen.
6. Mostly ovate to rarely trilobed foliage strongly colored with very dark mahogany.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
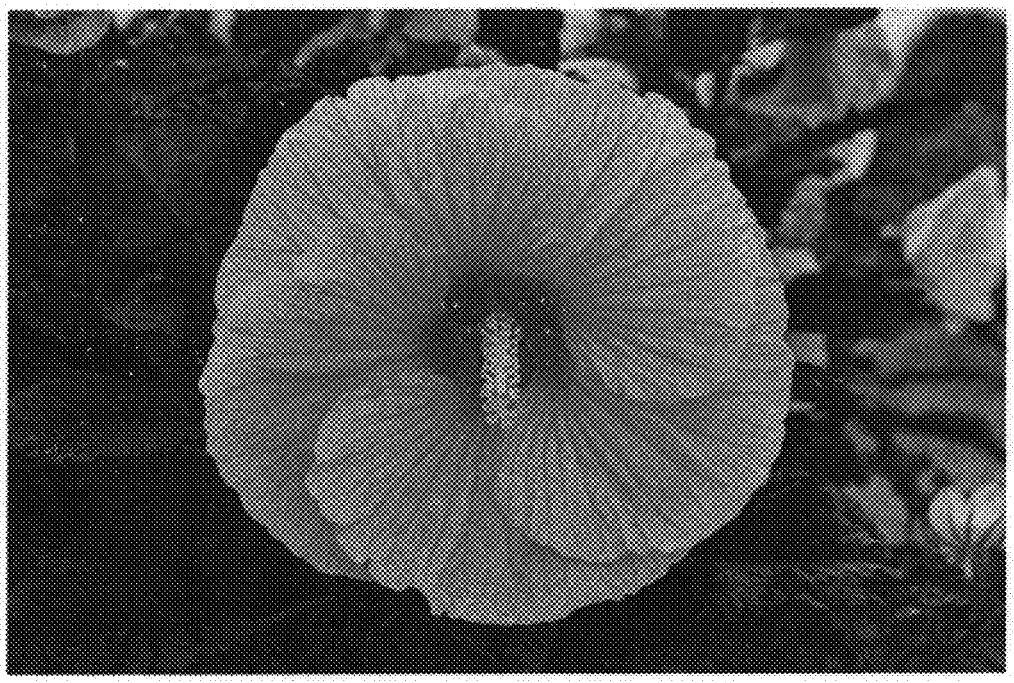
FIG. 1 shows a close-up of the flower and bud.
Figure 2:
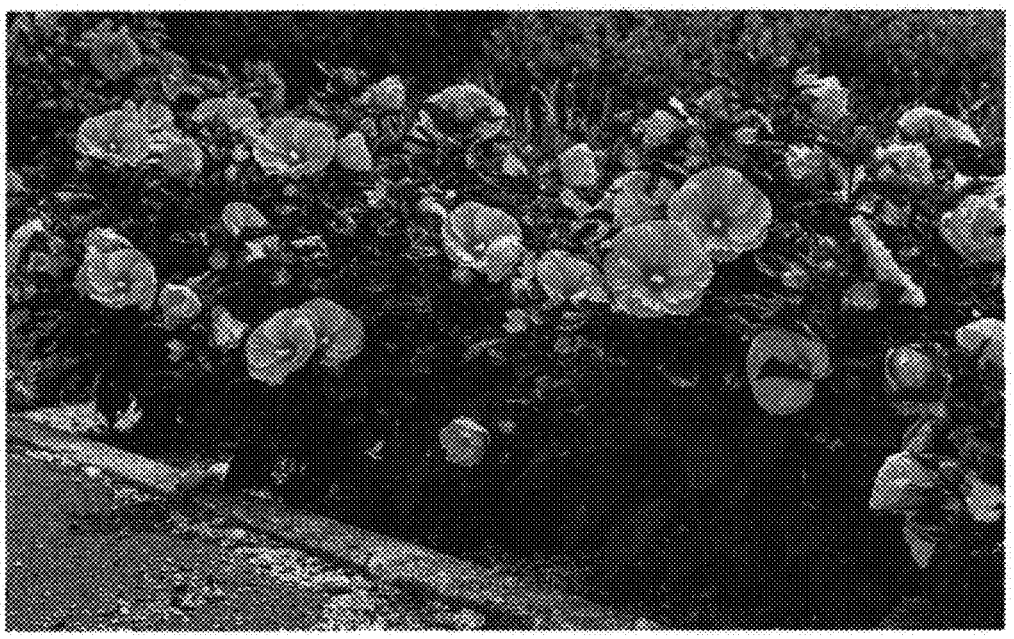
FIG. 2 shows a three-year-old plant in full flower in a display garden.
Figure 3:
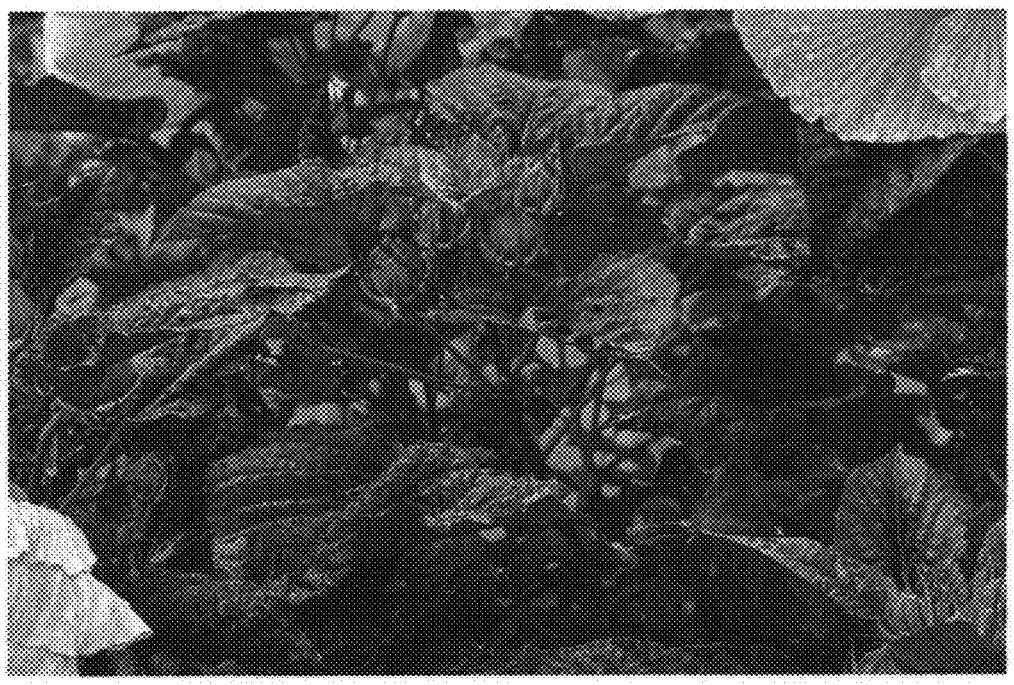
FIG. 3 shows the terminal foliage with stem and young flower buds.

The following descriptions and color references are based on the 2001 edition of The Royal Horticultural Society Colour Chart except where common dictionary terms are used. The new plant, *Hibiscus* 'Edge of Night', has not been observed under all possible environments. The phenotype may vary slightly with different environmental conditions, such as temperature, light, fertility, moisture and maturity levels, but without any change in the genotype. The following observations and size descriptions are of four-year-old plants in the loamy-sand, open-field full-sun trials of a nursery in Zeeland, Mich. with supplemental fertilizer and water as needed. The plants are of natural habit and were not treated with plant growth regulators, nor were they pinched at any time in the growth year.

Parentage: The parent is 15-117-4;

Propagation:

*Method.*—Shoot tip cuttings and sterile shoot-tip plant tissue culture division.

*Time to initiate roots from tissue culture.*—About two weeks.

*Rooting habit.*—Normal, branching, developing thick to about 2.2 cm diameter, fleshy.

*Root color.*—Creamy yellow, nearest RHS 161D depending on soil type.

*Crop time.*—Under normal summer growing conditions 12 to 16 weeks to flower in a four-liter container from cutting; plant vigor very good.

Plant description:

*Plant habit.*—Winter-hardy herbaceous perennial with about 51 thick, upright, heavily-branched stems producing an compact mound to about 94.0 cm tall and about 150.0 cm wide.

*Stem.*—Cylindrical, glabrous, glaucous; to about 94.0 cm tall and about 20.0 mm diameter at base, average about 90.0 cm tall and about 16.0 mm diameter at base.

*Stem color.*—Nearest RHS 138A proximally, distally nearest RHS 183C.

*Lateral branches.*—To 9 per stem, average about 6 per stem; cylindrical, glabrous, glaucous; to about 20.0 cm long and 5.0 mm diameter at base, smaller distally.

*Lateral branch color.*—Nearest RHS 138A proximally, distally nearest RHS 183C.

*Internode.*—About 30 nodes per stem below single flowers; average internode length about 2.6 cm of unpinched plant;

*Internode color.*—Same as surrounding stem; nearest RHS 138A proximally, distally nearest RHS 183C.

Foliage description: Typically ovate, rarely trilobed; alternate; apex narrowly acute; base rounded; margin coarsely and irregularly dentate; glabrescent abaxial and glabrous adaxial; adaxial surface lustrous when expanding, slightly lustrous when mature, abaxial surface matte; ovate leaf blades to about 15.5 cm long and about 12.0 cm across, trilobed leaf blades to about 14.5 cm long and about 13.5 cm wide, lobes to about 3.5 cm long; no fragrance detected;

*Foliage color.*—Young expanding leaves — adaxial between RHS 187A and RHS 187B, abaxial nearest RHS 137B; mature leaves — adaxial between RHS N186A and RHS 187A, abaxial nearest RHS 147B with edges moderately blushed with 187A.

*Veins.*—Palmate; glabrous; costate on abaxial.

*Vein color.*—Young adaxial midrib nearest RHS N186C with secondary veins between RHS 187B and 187A, abaxial young veins nearest RHS NN137D with a light blush of RHS 187C and midrib variable nearest RHS 187C and a blend between RHS 187A and RHS 181D; mature adaxial nearest RHS 187B both midrib and secondary veins and abaxial midrib between RHS 187C and RHS 187D secondary veins nearest RHS 187C.

*Petioles.*—Mostly cylindrical; glaucous; glabrous; to about 12.0 cm long and 5.0 mm diameter at base, average size about 8.5 cm long and 4.0 mm wide at base.

*Petiole color.*—Nearest blend between RHS 183B and RHS 183C above and nearest RHS 146C below and also proximally above.

Flower description: Complete; solitary; perfect; actinomorphic; mostly outward facing, with mostly outwardly facing outermost petals; rotate; lasting up to two days on plant; to about 19.5 cm across and slightly cupped petals and 6.5 cm deep, decreasing distally; with small eye zone relative to petal size;

*Buds one day prior to anthesis.*—Ellipsoidal with rounded apex and bluntly rounded base; sepals adpressed to petals; about 6.0 cm long and about 4.5 cm diameter in middle.

*Bud seven days prior to anthesis, with petals still enveloped in calyx.*—Cylindrical with pointed apex and rounded base; carinate at sepals fusion lines; glabrous, glaucous; about 2.6 cm long and about 1.9 cm across.

*Bud color one day prior to anthesis.*—Exposed petal color nearest RHS 64D with small blotchy portions nearest RHS 62D.

*Bud color seven days prior to anthesis.*—Nearest RHS 147C with light blushing at carinae nearest RHS 187B.

*Epicalyx*.—Typically 10 to 11 per flower; linear; entire; micro-puberulent adaxial and glabrate abaxial; with margin micro-ciliolate; dull surface abaxial and adaxial; narrowly acute apex and truncate base, distally arcuate toward center; to about 29.0 mm long and to about 5.0 mm wide at base.

*Epicalyx color*.—Adaxial nearest RHS 146C proximally and distally transitioning to nearest RHS 187B, abaxial base between RHS 145A and RHS 146D, center nearest RHS 137A, distally becoming nearest RHS 187A.

*Calyx*.—Star-shaped hypanthium; campanulate; 18.0 mm deep and 32.0 mm across.

*Sepals*.—Five, fused in basal 2.0 cm; acute apex; micro-puberulent adaxial and sparsely micro-puberulent abaxial; margin entire, edentate micro-ciliolate; abaxial and adaxial surfaces matte; individually about 40.0 mm long, about 25.0 mm wide at fusion.

*Sepal color*.—Adaxial base and primary veins nearest RHS 145D, distally nearest RHS 146B with light anthocyanin blush near margin of nearest RHS 187B; abaxial between RHS 144A and RHS 144B, distal veins and margins with light to medium anthocyanin nearest RHS 187B.

*Inflorescence*.—Flowering in the distal 30 cm; up to 45 total flowers per main stem without pinching, 19 on the upper unbranched portion and 26 in the lower branched portion.

*Flower lastingness*.—Persist for one to two days; effective for five to six weeks beginning late July.

*Flower fragrance*.—None detectable.

*Petals*.—Five; microscopically puberulent abaxial and adaxial, glabrous eye; adnate to the androecium to form a column, imbricate to about 60% overlapping at widest part (petals overlapping 60% to the petals on either side); palmately veined, primary veins impressed on adaxial and slightly costate abaxial; surface slightly dimpled; rounded with distinct claw and limb; margins: entire, edentate, micro-ciliolate; apex rounded; base short claw-like; petal undulation weak.

*Petal size*.—Average about 14.5 cm across and about 10.0 cm long, claw base about 8.0 mm across, smaller in later part of flowering season.

*Petal color*.—Adaxial central eye nearest RHS 53B, outer eye nearest RHS 53A, center petal nearest RHS 67C becoming blotched with between RHS 65D and RHS NN155D distally and toward margin, and veins of between RHS 61B and RHS 61B radiating from eye to the margin; abaxial basal 18 mm except margin nearest RHS NN155D, 15 mm of marginal 2.5 mm nearest RHS 61C, with distal center nearest RHS 64D and becoming mottled with nearest RHS NN155D toward base and margin, proximal veins nearest RHS NN155C and in distal center nearest RHS 64A.

*Flower lastingness*.—One to two days.

*Gynoecium*.—Single; partially enclosed in column; 60.0 mm long. Column: lustrous and glabrous, except basal 5.0 mm micro-puberulent; about 40.0 mm long and about 12.0 mm across at base; with pistil exserted about 12.0 mm; Column color: nearest RHS NN155C in central portion and nearest RHS 61B in distal 3.0 mm and striated with RHS 61B and RHS NN155C in basal 5.0 mm; Style: micro-puberulent in exserted region above column, glabrous below; about 53.0 mm long, penta-furcate in about distal 7.0 mm; branch diameter about 1.2 mm; color nearest RHS NN155B in region below split and split region nearest RHS N155B; Stigma: typically five; flattened globose, puberulent, about 3.0 mm in diameter and 1.5 mm tall; color nearest RHS 61B base and between RHS 70D RHS N155C; Ovary: superior, semi-globose to conical, rounded to broadly acute apex, flat truncate base; about 10.0 mm across at base and about 7.0 mm tall; deeply fissured; color nearest RHS 150D.

*Androecium*.—Filaments: numerous, about 120; about 3.0 mm long and about 0.2 mm diameter; attached along nearly the entire length of column; color nearest RHS NN155C. Anthers: flattened reniform; dorsifixed; about 2.5 mm long and 2.5 mm across and about 0.8 mm thick; color nearest RHS 11C; Pollen: abundant, globose, less than 0.1 mm long; color nearest RHS 11C.

Pedicel: Cylindrical; glabrous; glaucous; lustrous; length from base of sepal to abscission point about 27.0 mm long, from abscission point to stem node about 44.0 mm long; about 4.0 mm diameter at base and 5.0 mm diameter below sepals; decreasing in distal flowers;

Pedicel color: Nearest RHS 146C above abscission layer and between RHS 146C and RHS 183B below abscission layer;

Peduncle: Cylindrical, glabrous, glaucous; flowering in the distal 30.0 cm; color nearest RHS 183C distally and RHS 138A proximally;

Fruit: Penta-loculicidal capsule; pubescent along inner septa, glabrous outside; ellipsoidal, cuspidate apex and flattened base; about 22.0 mm long and 19.0 mm diameter; color nearest RHS N199B when mature;

Seed: Up to 48 per pod; minutely floccose; globose; about 3.0 mm in diameter; color nearest RHS N199B;

Resistance: *Hibiscus* 'Edge of Night' has not displayed any pest and disease resistance beyond that typical of hardy perennial *Hibiscus*.

Growing conditions: The plant grows best with plenty of moisture. Hardiness at least from USDA zone 4 through 9.

I claim:

1. A new cultivar of hardy herbaceous perennial *Hibiscus* hybrid plant named 'Edge of Night' as herein illustrated and described.

* * * * *